United States Patent [19]
Dugan

[11] Patent Number: 5,824,346
[45] Date of Patent: Oct. 20, 1998

[54] COMBINATION THERAPY FOR ADVANCED CANCER

[75] Inventor: Margaret H. Dugan, Woodside, N.Y.

[73] Assignee: Schering Corporation, Kenilworth, N.J.

[21] Appl. No.: 701,343

[22] Filed: Aug. 22, 1996

[51] Int. Cl.$^6$ .......................... A61K 31/33; A61K 33/24
[52] U.S. Cl. ............................. 424/649; 514/183
[58] Field of Search .............................. 514/183; 424/649

[56] References Cited

PUBLICATIONS

Piccioni et al., J. Chemother (Florence) (1995) 7(3) pp. 224–229 (Abstract only) Reference to Follow in Due Course.
Buziad, et al., Drug News and Perspectives (DN&P) 8 (8) pp. 480–485 (Oct., 1995.).
Anderson, et al., Oncology 9 (11) p. 1149ff. (Nov., 1995).
Pera, et al., Br. J. Cancer, 71 (5), pp. 904–906 (1995).
Bleehen, et al., Journal of Clinical Oncology, 13 (4), pp. 910–913 (Apr., 1995).
Newlands, Br. J. Cancer 65 (2), 287–291 (1992).
Rosenberg, et al., Nature 205 pp. 698–699 (1995).
Rosenberg, et al., Nature 222 pp. 385–386 (1972).
Piccioni, et al.; Cisplatin Increases Sensitivity of Human Luekiemic Blasts to Triazene Compounds; J. of Chemotherapy, vol. 7 –n. 3 (224–228) 1995.

*Primary Examiner*—Jerome D. Goldberg
*Attorney, Agent, or Firm*—Warrick E. Lee; Edward H. Mazer

[57] ABSTRACT

There is disclosed a method for treating advanced cancer in patients in need of such treating. Temozolomide and cisplatin are administered in combination in amounts sufficient to achieve a clinical response.

16 Claims, No Drawings

COMBINATION THERAPY FOR ADVANCED CANCER

Despite the numerous advances in cancer treatment, the well-known life style changes that can greatly reduce the risk of cancer, and the early warning signs that some cancers provide, many patients still develop advanced cancer for which no conventional therapies are available that offer any reasonable hope of cure or significant palliation. This invention is the use of two known anti-tumor agents in combination therapy to provide a positive effect on such advanced cancers. It is also expected that the combination therapy will allow the administration of the two anti-tumor agents in quantities that will not result in intolerable side effects.

Temozolomide is known for its anti-tumor effects. For example, in one study clinical responses were achieved in 17% of patients having advanced melanoma (Newlands ES, et al. Br J Cancer 65 (2) 287–2981, 1992). In another study a clinical response was achieved in 21% of patients with advanced melanoma (Journal of Clinical Oncology, Vol 13, No. 4 (April), 1995, pp 910–913). However, temozolomide has dose-limiting side effects, such as hematologic toxicity, myelosuppression, anemia, leukopenia, etc.

Cisplatin is known to have anti-tumor properties (see, for example B. Rosenberg et al. Nature 205, 698 (1965) and 222, 385 (1972). However, it too has dose-limiting side effects such as nephrotoxicity and ototoxicity.

There is a need for a method for treating advanced cancers with higher response rates or reduced side effects, or both.

SUMMARY OF THE INVENTION

This invention may be summarized as a method for treating advanced cancer in patients in need of such treating comprising administering temozolomide and cisplatin in amounts sufficient to achieve a clinical response. The temozolomide is administered to the patient in combination with the cisplatin, that is, the temozolomide and cisplatin doses are administered during the same period of time. Preferred specific dosing schedules are listed below.

DETAILED DESCRIPTION

All references cited herein are incorporated herein by reference.

The term "temozolomide" is intended to mean a compound having the formula.

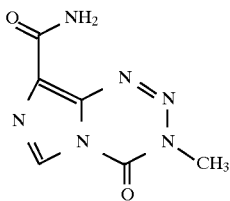

One chemical name for temozolomide is 3,4-dihydro-3-methyl-4-oxoimidazo-[5,1-d]1,2,3,4-tetrazin-8-carboximide. The synthesis of temozolomide is well known. See, for example, Stevens et al., J. Med. Chem, 1984, 27, 196–201 and Wang et al., J. Chem. Soc., Chem. Commun., 1994, pp 1687–1688.

Cisplatin (cis- diamminedichoroplatininum, Merck Index compound no. 319, 11th edition) has the formula

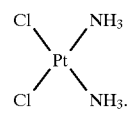

Advanced cancers treatable by this invention include malignant melanoma, malignant metastasized melanoma, cancer of the lung, cancer of the breast, brain cancer, ovarian cancer, cancer of the head and/or neck, sarcoma, prostate cancer, and other cancers known to be at least partially responsive to cisplatin treatment, that have advanced to a stage where conventional therapy is unlikely to provide a cure.

A person suffering from advanced cancer may exhibit one or more of the following signs or symptoms:
(a) presence of cancerous tumor,
(b) fatigue,
(c) pain,
(d) decreased performance status from tumor burden, and
(e) the well known symptoms associated with each specific cancer.

To practice the invention, temozolomide and cisplatin are administered to the patient exhibiting one or more of the above signs or symptoms in amounts sufficient to eliminate or at least alleviate one or more of the signs or symptoms.

The preferred dosage of temozolomide for practicing the combination therapy of this invention is 50 to 400 mg per $m^2$ of the patient's body surface area per day, more preferably 75 to 300 $mg/m^2$ and most preferably 100 to 200 $mg/m^2/day$. It is preferred that the daily dosage of temozolomide be administered once per day for a 2 to 10 day period, more preferably for a 3 to 8 day period and most preferably for a 5 day period.

Alternatively the temozolomide may be administered for a much longer period at reduced dosage. For example, the temozolomide could be administered daily for 11 days to six weeks at a dosage of 50 to 150 $mg/m^2/day$.

Temozolomide may be administered orally in capsule form wherein it is admixed with conventional pharmaceutical carriers. Preferred temozolomide capsule formulations are:

| Ingredient | mg/Capsule | | | |
|---|---|---|---|---|
| temozolomide | 5 | 20 | 100 | 250 |
| Anhydrous Lactose NF | 132.8 | 182.2 | 175.7 | 154.3 |
| Sodium Starch Glycolate NF | 7.5 | 11.0 | 15.0 | 22.5 |
| Colloidal Silicon Diozide NF | 0.2 | 0.2 | 0.3 | 0.7 |
| Tartaric Acid NF | 1.5 | 2.2 | 3.0 | 9.0 |
| Steric Acid NF | 3.0 | 4.4 | 6.0 | 13.5 |
| Capsule Size* | 3 | 2 | 1 | 0 |

*White opaque, preservative-free, two-piece hard gelatin capsules

It is especially preferred that the patient fast from all food or drink, except water, for four hours before temozolomide administration and for two hours after.

The cisplatin is preferably administered with a single intravenous infusion on day one of the temozolomide administration period about four hours after the first day's administration of temozolomide. To maintain sufficient hydration, one liter of normal saline with 20 meq KCl/L and 1 gm of magnesium sulfate, at a rate of about 250 ml/hour is administered prior to and after the cisplatin infusion. The amount of cisplatin in the infusion is preferably 25 to 300 mg per $m^2$ of the patient's body surface area, more preferably 50 to 150 $mg/m^2$ and most preferably 75 to 100 $mg/m^2$.

Additional fluid may be given to maintain adequate urine output. The cisplatin is preferably administered with 500 ml of normal saline containing 12.5 gm mannitol over a one hour period.

Alternatively the a dosage of cisplatin listed in the above paragraph could be administered over a 2 to 5 day period. Up to 100 mg/day/m$^2$ of patent's body surface area could be administered daily for 5 consecutive days.

After a period of about 28 to 42 days, preferably 28 days, from the first day of the temozolomide administration period, another administration cycle may be performed, with temozolomide being administered on day one and on each subsequent day of the administration period and cisplatin being administered on day one, or less preferably over a period of 2 to 5 days. For example, for a five-day temozolomide administration period, a one-day cisplatin administration period, and a 28 day treatment cycle, the treatment will take place for five days (temozolomide treatment on days 1 to 5 and cisplatin treatment on day 1), followed by 28−5=23 days during which no treatment is given, followed by five more days of treatment as the start of the second cycle.

The treatment cycles may be continued until a clinical response is achieved or until intolerable side effects are encountered. The dosages of temozolomide and/or cisplatin may be increased with each new treatment cycle, provided intolerable side effects are not encountered. The dosages may also be decreased, if intolerable side effects are encountered. It is presently preferred to gradually adjust the dosage of temozolomide while holding the cisplatin dosage constant.

A common, but tolerable side effect of both temozolomide and cisplatin is nausea and vomiting. This can be alleviated by administering an anti-emetic in conjunction with the temozolomide. It is preferred that the anti-emetic Ondansetron be given p.o. in a dose of about 8 mg about 30 minutes before temozolomide administration. Likewise it is preferred to administer Ondansetron 32 mg IV or Granisetron 1 mg IV and Decadron 10 mg IV about 30 before the cisplatin infusion. Of course other anti-emetics such as Haldol, Benadryl, and Ativan may also be used as needed.

Of course, other forms of administration of both active ingredients, as they become available, are contemplated, such as by nasal spray, transdermally, by suppository, by sustained release dosage form, by IV injection, etc. Any form of administration will work so long as the proper dosages are delivered without destroying the active ingredient.

The effectiveness of treatment may be determined by controlled clinical trials. Patients having advanced cancer with measurable or evaluable tumors will be included in the study. A measurable tumor is one that can be measured in at least two dimensions such as a lung tumor surrounded by aerated lung, a skin nodule, or a superficial lymph node. An evaluable tumor in one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to provide an evaluable disease, such as PSA for prostate cancer, CA-125 for ovarian cancer, CA-15-3 for breast cancer, etc.

The tumor will be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25 % increase in the sum of the diameters of all tumors. For (a) and (b) no new tumors should appear.

No clinical response, i.e. progressive disease in defined as an increase of more than 50% in the product of the largest perpendicular diameters for at least one bidimensionally measurable tumor, or an increase of more than 25% in measurable dimension of at least one unidimensionally measurable tumor.

For patients having both uni- and bi-dimensionally measurable tumors, the overall response will be determined in accordance with the following table.

| Response in bidimensionally measurable disease | Response in unidimensionally measurable disease | Overall Response |
| --- | --- | --- |
| PD | any | PD |
| Any | PD | PD |
| SD | SD or PR | SD |
| SD | CR | PR |
| PR | SD or PR or CR | PR |
| CR | SD or PR | PR |
| CR | CR | CR |

Abbreviations:
PD: Progressive Disease
CR: Complete Response
PR: Partial Response
SD: Stable Disease Of course elimination or alleviation of other known signs or symptoms of advanced cancer, especially those listed previously can also be used to evaluate the effectiveness of this invention.

The advanced cancers should be evaluated, i.e. tumors measured, etc., no more than 14 days before the start of the treatment. These cancers should be reevaluated about 28 days after day 1 of administration of the first dose of temozolomide and cisplatin. Twenty eight days after this initial administration another administration period may be performed, and evaluations performed 28 days after the start of this second cycle. The treatment cycles may be continued until a clinical response is achieved or unacceptable toxicity is encountered.

Another aspect of this invention is the treatment of advanced cancer with reduced side effects normally associated with temozolomide and cisplatin. It is believed that this objective can be achieved by administration of lower doses of the two active ingredients or by shorter duration of dosing brought about by the synergistic effect of the combination.

The most serious side effect of temozolomide is hematologic toxicity. Dose limiting toxicity for temozolomide is defined herein as CTC Grade 4 neutropenia (absolute neutrophil count, including bands, of less than $0.5 \times 10^3/mm^3$) which is not resolved in five days or CTC Grade 4 anemia (hemoglobin of less than 6.5 g/dl), or CTC Grade 3 thrombocytopenia (platelet count of less than $50 \times 10^3/mm^3$) or CTC Grade 4 thrombocytopenia (platelet count of less than $25 \times 10^3/mm^3$).

The most common side effect of cisplatin is nephrotoxicity. Dose limiting toxicity would cause serum creatinine of more than 2.2 mg/dL persisting for more than 2 weeks from the time of dosing.

I claim:

1. A method for treating advanced cancer sensitive to the combination below in patients in need of such treatment comprising administering temozolomide and cisplatin wherein the amount of temozolomide administered is from 50 to 400 mg per $m^2$ of the patients body surface area per day for a period of from 2 to 10 days and the amount of cisplatin administered is from 25 to 300 mg per $m^2$ of the patients body surface area as a single dose on the first day of temozolomide administration.

2. The method of claim 1 wherein beginning 28 to 42 days after the first day of the temozolomide administration period, the temozolomide and cisplatin administrations are repeated.

3. The method of claim 1 wherein the amount of temozolomide administered is from 75 to 300 mg per $m^2$ of the patient's body surface area per day for a period of from 3 to 8 days and the amount of cisplatin administered is from 50 to 150 mg per $m^2$ of the patients body surface area as a single dose on the first day of temozolomide administration.

4. The method of claim 3 wherein beginning about 28 to 35 days after the first day of the temozolomide administration period, the temozolomide and cisplatin administrations are repeated.

5. The method of claim 3 wherein the amount of temozolomide administered is from 100 to 200 mg per $m^2$ of the patient's body surface area per day for a period of 5 days and the amount of cisplatin administered is from 75 to 100 mg per $m^2$ of the patients body surface area as a single dose on the first day of temozolomide administration.

6. The method of claim 5 wherein beginning 28 days after the first day of the temozolomide administration period, the temozolomide and cisplatin administrations are repeated.

7. The method of claim 1 wherein the temozolomide is administered orally after the patient has fasted from food and liquids other than water for 4 hours before temozolomide administration and for 2 hours after temozolomide administration, and the cisplatin is administered by intravenous infusion.

8. The method of claim 1 wherein the temozolomide is administered orally after the patient has fasted from food and liquids other than water for 4 hours before temozolomide administration and for 2 hours after temozolomide administration, and the cisplatin is administered by intravenous infusion.

9. The method of claim 2 wherein the temozolomide is administered orally after the patient has fasted from food and liquids other than water for 4 hours before temozolomide administration and for 2 hours after temozolomide administration, and the cisplatin is administered by intravenous infusion.

10. The method of claim 3 wherein the temozolomide is administered orally after the patient has fasted from food and liquids other than water for 4 hours before temozolomide administration and for 2 hours after temozolomide administration, and the cisplatin is administered by intravenous infusion.

11. The method of claim 4 wherein the temozolomide is administered orally after the patient has fasted from food and liquids other than water for 4 hours before temozolomide administration and for 2 hours after temozolomide administration, and the cisplatin is administered by intravenous infusion.

12. The method of claim 5 wherein the temozolomide is administered orally after the patient has fasted from food and liquids other than water for 4 hours before temozolomide administration and for 2 hours after temozolomide administration, and the cisplatin is administered by intravenous infusion.

13. The method of claim 6 wherein the temozolomide is administered orally after the patient has fasted from food and liquids other than water for 4 hours before temozolomide administration and for 2 hours after temozolomide administration, and the cisplatin is administered by intravenous infusion.

14. The method of claim 1 wherein the temozolomide is administered orally for a period of from 6 days to six weeks.

15. The method of claim 1 wherein the cisplatin is administered by intravenous infusion over a period of 2 to 5 days.

16. The method of claim 15 wherein the temozolomide is administered orally for a period of from 6 days to six weeks.

* * * * *